US008920331B2

(12) United States Patent
Ouchi et al.

(10) Patent No.: US 8,920,331 B2
(45) Date of Patent: Dec. 30, 2014

(54) PULSE WAVE MEASURING DEVICE

(75) Inventors: Kazushige Ouchi, Saitama (JP); Takuji Suzuki, Yokohama (JP); Kenichi Kameyama, Kawasaki (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 1248 days.

(21) Appl. No.: 12/341,225

(22) Filed: Dec. 22, 2008

(65) Prior Publication Data
US 2009/0182239 A1  Jul. 16, 2009

(30) Foreign Application Priority Data
Dec. 27, 2007  (JP) .................................. 2007-337135

(51) Int. Cl.
*A61B 5/02* (2006.01)
*A61B 5/024* (2006.01)
*A61B 5/00* (2006.01)

(52) U.S. Cl.
CPC ........... *A61B 5/02438* (2013.01); *A61B 5/6826* (2013.01); *A61B 5/6838* (2013.01); *A61B 5/02433* (2013.01)
USPC .......................................... 600/500; 600/501

(58) Field of Classification Search
None
See application file for complete search history.

(56) References Cited

U.S. PATENT DOCUMENTS

2006/0206019 A1*  9/2006  Zhang et al. ................... 600/323
2009/0247885 A1   10/2009  Suzuki et al.
2009/0247886 A1   10/2009  Ouchi et al.

FOREIGN PATENT DOCUMENTS

| JP | 57-142236 A | 9/1982 |
|---|---|---|
| JP | 57-185306 U | 11/1982 |
| JP | 59-22537 A | 2/1984 |
| JP | 2000-97893 A | 4/2000 |
| JP | 2001-70266 A | 3/2001 |
| JP | 2003-169780 | 6/2003 |
| JP | 2004-201868 A | 7/2004 |
| JP | 2005-270544 A | 10/2005 |
| JP | 2006-33127 | 2/2006 |
| JP | 2006-80816 | 3/2006 |
| JP | 2006-204436 A | 8/2006 |
| JP | 2006-288619 A | 10/2006 |
| JP | 2007-319232 A | 12/2007 |

OTHER PUBLICATIONS

U.S. Appl. No. 12/167,586, filed Jul. 3, 2008, Kazushige Ouchi, et al.
Japanese Office Action issued Jul. 31, 2012 in Patent Application No. 2007-337135 with English Translation.
Office Action issued Feb. 26, 2013 in Japanese Patent Application No. 2007-337135 with English language translation.

* cited by examiner

*Primary Examiner* — Benjamin P Blumel
(74) *Attorney, Agent, or Firm* — Oblon, Spivak, McClelland, Maier & Neustadt, L.L.P.

(57) ABSTRACT

According to the invention, a pulse wave measuring device includes: a connector that is disposed on a main unit; an external sensor that includes an external light-emitting module radiating light to a human body to be measured and an external light-receiving module receiving at least one of reflected light and transmitted light originating from the external light-emitting module and the human body so as to measure a pulse wave; an first controller that switches the external light-emitting module ON and OFF; a second controller that switches the external light-receiving module ON and OFF; and an external sensor connection determination section that determines a connection between the external sensor and the connector in accordance with a transient response of the external light-receiving module, wherein, after the external sensor connection determination section determines that the external sensor is connected to the connector, a measurement of the pulse wave by using the external sensor is started.

4 Claims, 12 Drawing Sheets

PULSE WAVE MEASURING DEVICE

CROSS-REFERENCE TO RELATED APPLICATIONS

This application is based upon and claims the benefit of priority from Japanese Patent Application No. 2007-337135, filed Dec. 27, 2007, the entire contents of which are incorporated herein by reference.

BACKGROUND

1. Field

The present invention relates to a pulse wave measuring device for measuring a pulse wave while being put on a human body.

2. Description of the Related Art

One of devices that measure vital-sign information about a user while being put on a body, such as a wrist, is a pulse wave measuring device that optically measures a pulse wave.

A pulse wave is a waveform arising when a change in the pressure of blood stemming from contraction of the heart travels to peripheral blood vessels, and the waveform is primarily induced by a change in the flow of arterial blood. However, amounts of hemoglobin in blood acquired at an area to be measured also change in the same manner as does the flow of arterial blood, and hence a pulse wave can be measured by means of measuring the amounts of hemoglobin.

One technique for measuring a pulse wave is a photoelectric pulse wave detection method. A light absorption factor of hemoglobin changes depending on the wavelength of light. Light in a waveband (ranging from visible light to near infrared light), which is absorbed by hemoglobin, is radiated from a light-emitting element (LED: a light-emitting diode, and the like). Differences in the intensity of reflected light or transmitted light induced by a change in blood flow are detected by a light-receiving element (a photodiode, and the like), thereby detecting a pulse wave.

Depending on a waveband to be used, a change in blood flow of an arteriole near skin is captured by means of pulse wave detection complying with the photoelectric pulse wave detection method; hence, pulse wave measurement is suitable for measurement performed in an area (a finger, a palm, an ear lobe, and the like) where a plurality of arterioles are present. (For example, refer to JP-A-2003-169780 (KOKAI)).

A device for measuring a pulse wave without placing a burden on the user in a daily life has already been put into commercial production. For instance, a main unit of a pulse wave measuring device is put on a wrist like a wrist watch, and only a pulse wave sensor is withdrawn from the main unit by means of a cable. The pulse wave sensor is wrapped around a finger, to thus measure a pulse wave in a palm. However, wrapping the pulse wave sensor around a finger hinders daily living activities, such as washing hands and gripping an object. For this reason, it is desirable to measure a pulse wave at a wrist where the main unit of the pulse wave measuring device is put. However, signal intensity acquired through photoelectric pulse wave measurement performed at a wrist is weaker than that acquired through measurement performed in a palm, and there is the case where measurement cannot be performed stably depending on the user or a state.

In a pulse wave measurement device that enables selective use of a removable pulse wave sensor for finger use and a wrist pulse wave sensor for measuring a pulse wave at a wrist, it is laborious for the user to specify and switch the pulse wave sensor to be used for measurement.

Therefore, it is appropriate that the pulse wave measuring device should determine connection/disconnection of the finger pulse wave sensor and automatically switch operation of the pulse wave measuring device so as to measure a pulse wave at a finger when the finger pulse wave sensor is connected and at a wrist when the finger pulse wave sensor is not connected.

It is conceivable that an electrical connection detection mechanism will be provided in a connector for detecting connection of the finger pulse wave sensor. Proposed as such is a mechanism having a logical output circuit using; for instance, a GND pin provided in a cable terminal, thereby detecting connection/disconnection of an external input device (see; for instance, JP-A-2006-33127(KOKAI)). Provision of a mechanical connection detection mechanism is also conceivable. For instance, a connector equipped with a contact switch for detecting connection is proposed (see; for instance, JP-A-2006-80816(KOKAI)).

However, miniaturizing the connector of the pulse wave measuring device of wrist watch type as small as possible is desirable.

When the detection technique, such as that described in connection with JP-A-2006-33127(KOKAI), is adopted, provision of an electrode for detecting connection is required, which results in an increase in the number of electrodes as well as the number of signal lines and an increase in the size of the connector.

When the detection technique, such as that described in connection with JP-A-2006-80816(KOKAI), is adopted, a mechanical mechanism is provided; hence, there is a disadvantage of requirement of a space for the mechanism and complication of the mechanism itself.

SUMMARY OF THE INVENTION

According to an aspect of the present invention, there is provided a pulse wave measuring device including: a main unit; a connector that is disposed on the main unit; an external sensor that includes an external light-emitting module emitting light to a human body to be measured and an external light-receiving module receiving at least one of reflected light and transmitted light originating from the external light-emitting module and the human body so as to measure a pulse wave; an first controller that controls the external light-emitting module; an second controller that controls the external light-receiving module; and an external sensor connection determination section that determines a connection between the external sensor and the connector in accordance with a transient response of the external light-receiving module, the transient response being produced by activation of the external light-emitting module and the external light-receiving module, wherein, after the external sensor connection determination section determines that the external sensor is connected to the connector, a measurement of the pulse wave by using the external sensor is started.

BRIEF DESCRIPTION OF THE SEVERAL VIEWS OF THE DRAWINGS

A general architecture that implements the various feature of the invention will now be described with reference to the drawings. The drawings and the associated descriptions are provided to illustrate embodiments of the invention and not to limit the scope of the invention.

DETAILED DESCRIPTION

Figure 1:
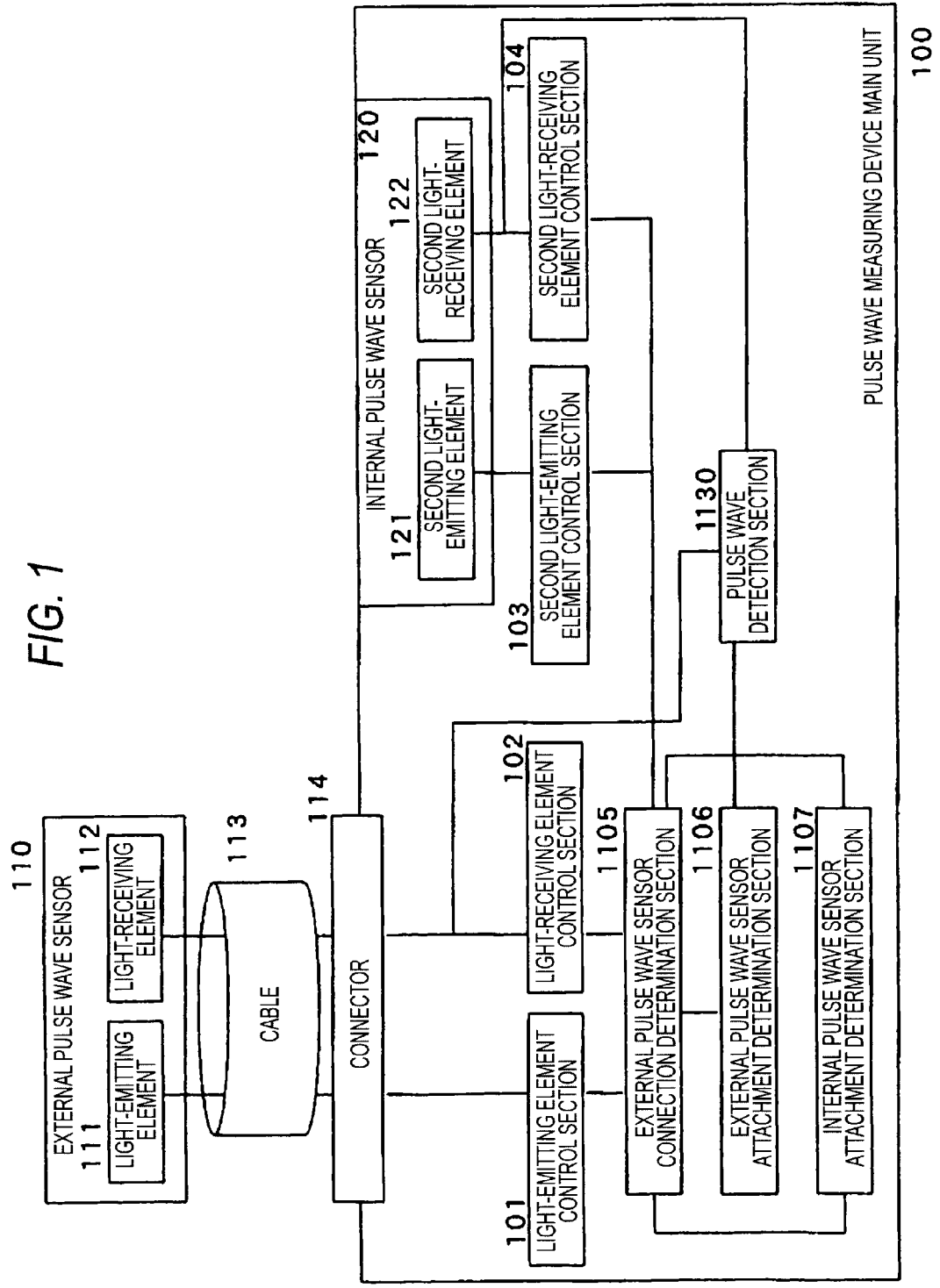
FIG. 1 is a block diagram showing the functional configuration of an exemplary pulse wave measuring device of an embodiment of the present invention.

The best mode for implementing a pulse wave measuring device of the present invention will be described below by reference to the drawings. Throughout the drawings, like areas are assigned like reference numerals, and overlapping explanations are omitted.

FIG. 1 is a block diagram showing the functional configuration of a pulse wave measuring device of an embodiment of the present invention.

As shown in FIG. 1, a pulse wave measuring device broadly includes a pulse wave measuring device main unit 100 incorporating a control section and a determination section (both of which will be described later), an external pulse wave sensor 110, and an internal pulse wave sensor 120 built in the pulse wave measuring device main unit 100.

The external pulse wave sensor 110 is connected to the pulse wave measuring device main unit 100 by way of a cable 113 and a connector 114. The external pulse wave sensor 110 incorporates a light-emitting element 111 that radiates light of given intensity (light including; for instance, infrared light) to an area to be measured and a light-receiving element 112 that receives the light, which has been radiated by the light-emitting element 111 and reflected from the area to be measured, and converts the received light into an electric signal.

The light-emitting element 111 and the light-receiving element 112 are connected to the cable 113 and further connected to a connector 114 provided in the pulse wave measuring device main unit 100 by way of the cable 113. A signal output from the light-receiving element 112 is input to a pulse wave detection section 130, where a pulse interval is detected from a pulse wave signal that is generated by extracting, amplifying, and shaping a photoelectric pulse wave component.

An internal pulse wave sensor 120 built in the pulse wave measuring device main unit 100 has a second light-emitting element 121 that radiates light of given intensity (light including; for instance, infrared light) to an area to be measured and a second light-receiving element 122 that receives light, which has been radiated by the second light-emitting element 121 and reflected from the area to be measured, and converts the received light into an electric signal. A signal output from the second light-receiving element 122 is input to the pulse wave detection section 130, where a pulse interval is detected from a pulse wave signal that is generated by extracting, amplifying, and shaping a photoelectric pulse wave component.

A light-emitting element control section 101, a light-receiving element control section 102, a second light-emitting element control section 103, a second light-receiving element control section 104, an external pulse wave sensor connection determination section 105, an external pulse wave sensor attachment determination section 106, and an internal pulse wave sensor attachment determination section 107 are provided in the pulse wave measuring device main unit 100.

The light-emitting element control section 101 is connected to the light-emitting element 111 by way of the connector 114 and the cable 113, thereby controlling operation of the light-emitting element 111; and sends an electric signal to the light-emitting element 111.

Likewise, the light-receiving element control section 102 is connected to the light-receiving element 112 by way of the connector 114 and the cable 113; controls operation of the light-receiving element 112; and receives the electric signal from the light-receiving element 112.

The light-emitting element control section 101 and the light-receiving element control section 102 are connected to the external pulse wave sensor connection determination section 105, respectively, and determine the state of connection of the external pulse wave sensor 110. Further, determination information from the external pulse wave sensor connection determination section 105 is transmitted to the external pulse wave sensor attachment determination section 106 and determines the state of attachment of the external pulse wave sensor 110. Further, determination information from the external pulse wave sensor connection determination section 105 is transmitted to the internal pulse wave sensor attachment determination section 107, as well.

The second light-emitting element 121 is connected to the second light-emitting element control section 103, and the function of the second light-emitting element is controlled. Likewise, the second light-receiving element 122 is connected to the second light-receiving element control section 104, and the function of the second light-receiving element is controlled, and an electric signal from the second light-receiving element 122 is received.

The second light-emitting element control section 103 and the second light-receiving element control section 104 are connected to the external pulse wave sensor connection determination section 105, respectively.

Figure 2:
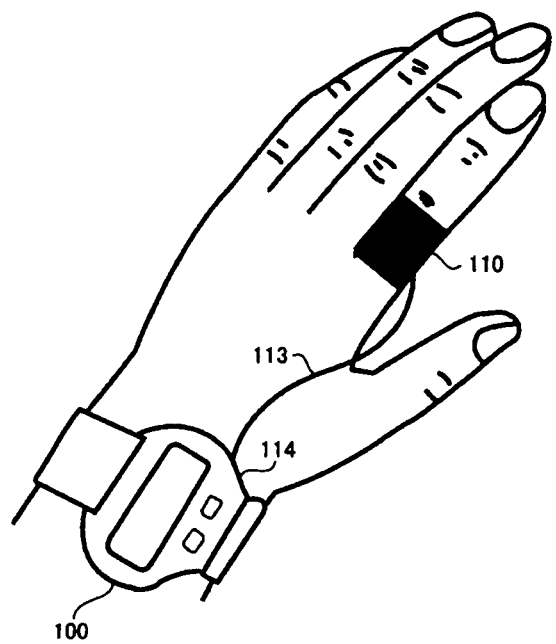
FIG. 2 is an exemplary schematic view showing example attachment of the pulse wave measuring device of the embodiment of the present invention.
Figure 3:
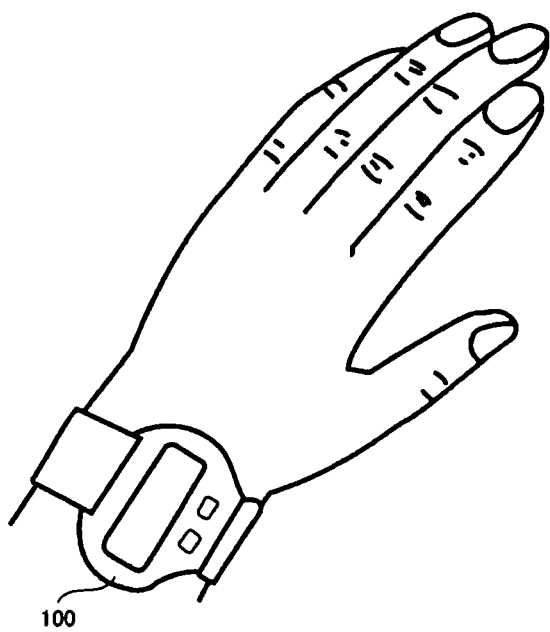
FIG. 3 is an exemplary schematic view showing example attachment of the pulse wave measuring device of the embodiment of the present invention.

FIGS. 2 and 3 are diagrammatic views showing an example of attachment of the pulse wave measuring device of the embodiment of the present invention. FIG. 2 shows an example in which a pulse wave is measured at the thick of a finger with the pulse wave measuring device main unit 100 put on a wrist and the external pulse wave sensor 110 put on a finger. FIG. 3 shows an example in which a pulse wave is measured at a wrist by the internal pulse wave sensor 120 while the pulse wave measuring device main unit 100 is put on the wrist.

Figure 4:
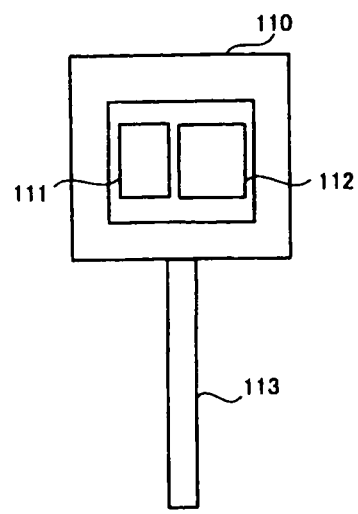
FIG. 4 is an exemplary schematic view showing an example configuration of an external pulse wave sensor of the embodiment of the present invention.

In the external pulse wave sensor 110, the light-emitting element 111 and the light-receiving element 112 are arranged side by side as shown in FIG. 4. The sensor is wrapped around the forefinger, and the like, by means of a belt (not shown); for instance, a Hook-and-Loop fastener, and a pulse wave is measured at the thick of the forefinger.

Figure 5:
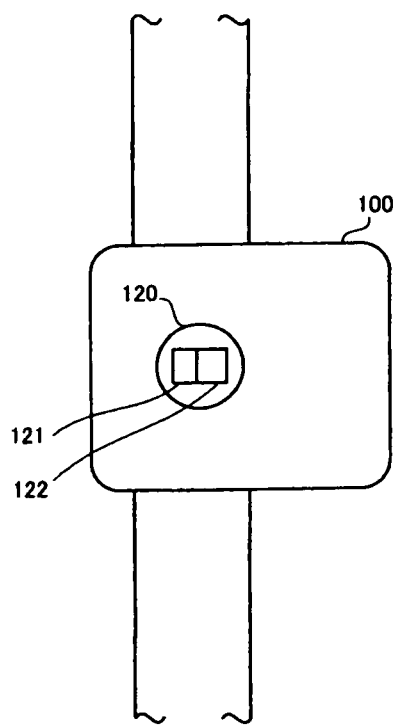
FIG. 5 is an exemplary schematic view showing an example configuration of an internal pulse wave sensor of the embodiment of the present invention.

In the internal pulse wave sensor 120, the second light-emitting element 121 and the second light-receiving element 122 are arranged side by side on the back of the pulse wave measuring device main unit 100 as shown in FIG. 5. The internal pulse wave sensor 120 measures a pulse wave at the wrist contacting the back of the pulse wave measuring device main unit 100.

The light-emitting element 111 and the second light-emitting element 121 radiate light in a waveband at which hemoglobin exhibits an 2 characteristic (visible light to near infrared light) to a skin that is an area to be measured, and the light-receiving element 112 or the second light-receiving element 122 detects differences in intensity of reflected light or transmitted light induced by a change in blood flow. Accordingly, the light-receiving element 112 preferably has a characteristic that exhibits superior sensitivity at a peak wavelength of light emitted by the light-emitting element 111, and the second light-receiving element 122 preferably has a characteristic that exhibits superior sensitivity at a peak wavelength of light emitted by the second light-emitting element 121. The light-emitting element 111 and the second light-emitting element 121 preferably use a light-emitting diode, and the like; and the light-receiving element 112 and the second light-receiving element 122 preferably use a photodiode, a phototransistor, and the like. However, other light-emitting means and light-receiving means may also be used.

Figure 6:
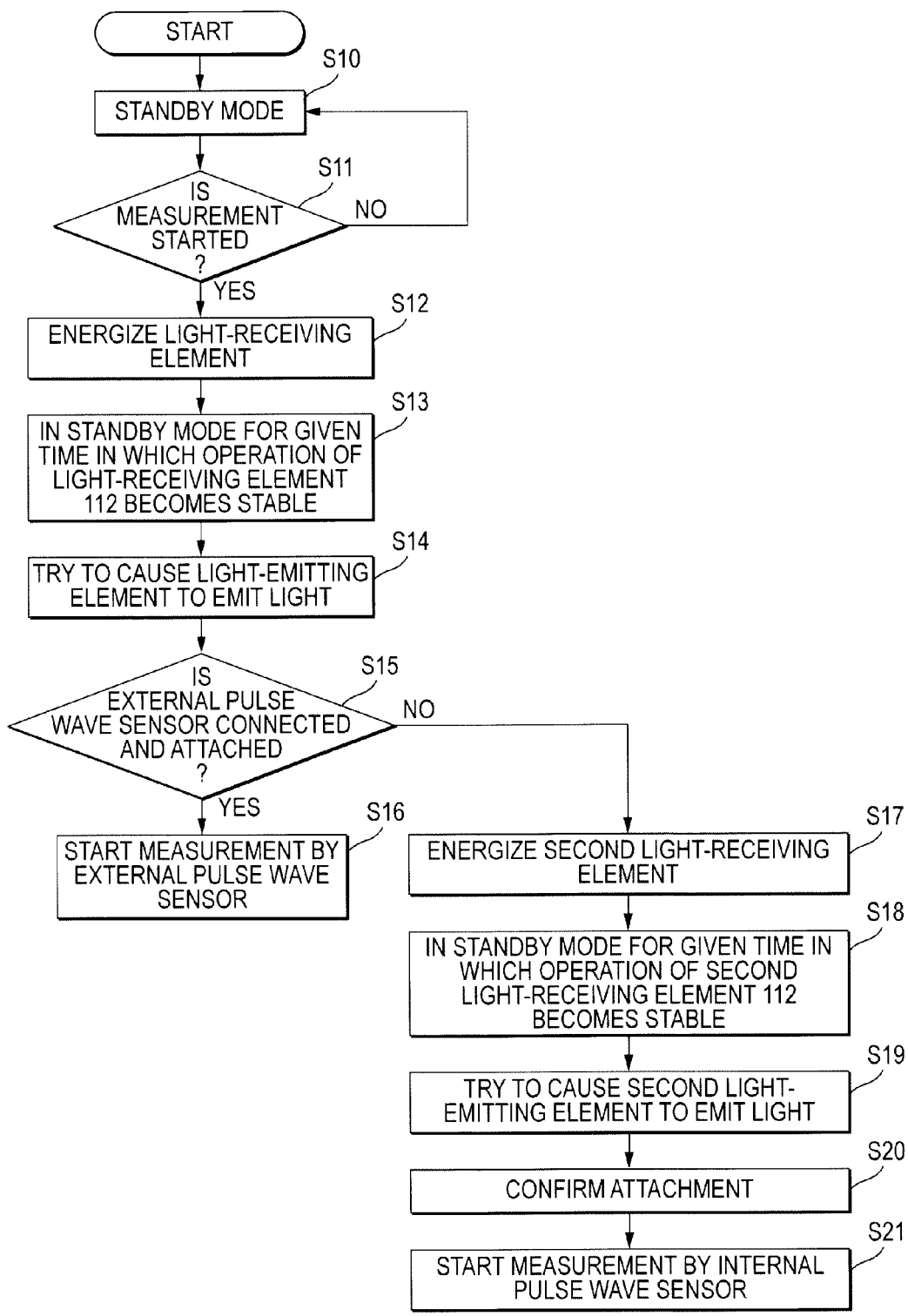
FIG. 6 is an exemplary flowchart showing processing operation of the embodiment of the present invention.

FIG. 6 is a flowchart for describing processing operation of the pulse wave measuring device of the embodiment of the present invention. Descriptions are provided hereinbelow along the flowchart.

First, when the power of the pulse wave measuring device is turned on, the device is started in a standby mode (step S10). When the user presses a measurement start button (not shown) provided on the pulse wave measuring device to perform measurement initiation operation (step S11), the light-receiving element control section 102 energizes the light-receiving element 112 to turn on the light-receiving element 112 (step S12). When preliminary energization is unnecessary to activate of the light-receiving element 112, processing with respect to step S12 may be omitted.

Next, the pulse wave measuring device is in the standby mode for a given time in which the operation of the light-receiving element 112 becomes stable (step S13). When the light-receiving element 112 to be used does not need a wait time before achieving stability, processing with respect to step S13 may be omitted.

The light-emitting element control section 101 sends the electric signal; and tries to cause the light-emitting element 111 to emit light (step S14). By means of reaction of the light-receiving element 112 caused after emission of light from the light-emitting element 111, the external pulse wave sensor connection determination section 105 and the external pulse wave sensor attachment determination section 106 determine connection and attachment of the external pulse wave sensor 110 (step S15).

When the external pulse wave sensor 110 is determined to be connected, the external pulse wave sensor 110 receives the electric signal; and starts measuring a pulse wave (step S16).

In the meantime, when the external pulse wave sensor 110 is determined not to be connected, the light-emitting element control section 101 stops sending the electric signal to the connector 114 for connecting the light-emitting element 111, and the light-receiving element control section 102 stops receiving the electric signal from the connector 114 for connecting the light-receiving element 112.

Subsequently, the second light-receiving element control section 104 energizes the second light-receiving element 122, thereby turning on the second light-receiving element 122 (step S17). When preliminary energization is unnecessary at the time of activation of the second light-receiving element 122, processing pertaining to step S17 can be omitted.

The pulse wave measuring device is in a standby mode for a given time in which the operation of the second light-receiving element 122 becomes stable after being energized (step S18). When the second light-receiving element 122 does not need a wait time before achieving stability, processing pertaining to step S18 may be omitted.

The second light-emitting element control section 103 sends the electric signal; and tries to cause the second light-emitting element 121 to emit light (step S19). By means of reaction of the second light-receiving element 122 caused after emission of light from the second light-emitting element 121, the internal pulse wave sensor attachment determination section 107 determines whether or not the pulse wave measuring device main unit 100 is properly attached (step S20).

After confirming that the pulse wave measuring unit is attached to the main unit, the internal pulse wave sensor 120 measures a pulse wave (step S21).

(Determination as to the Connection-and-Attachment of the External Pulse Wave Sensor)

Figure 7:
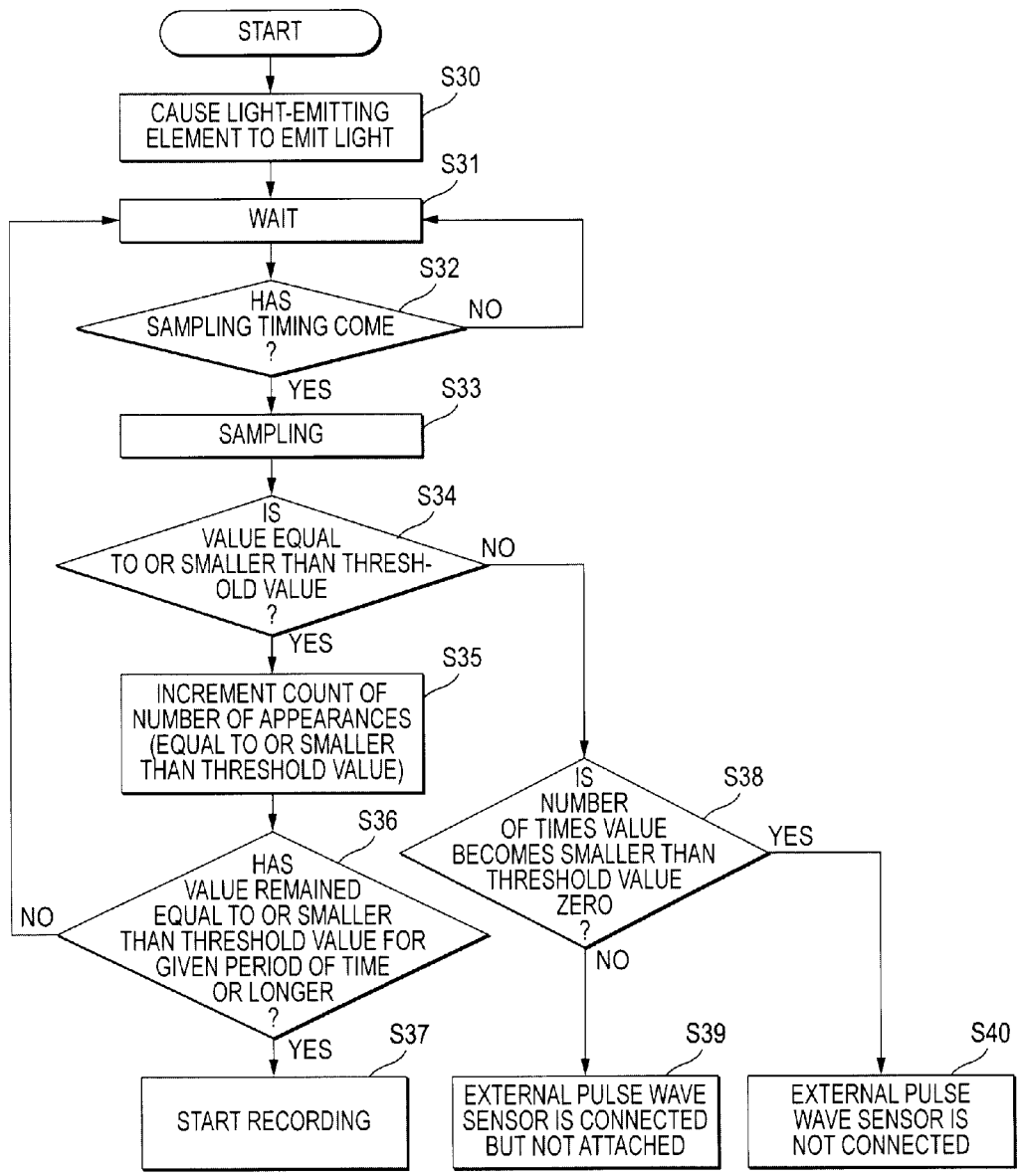
FIG. 7 is an exemplary flowchart showing processing operation of the embodiment of the present invention.

Next, processing operation of the external pulse wave sensor connection determination section 105 and processing operation of the external pulse wave sensor attachment determination section 106 (step S15 and the like) will be described in detail along a flowchart shown in FIG. 7.

After emitting of the light-emitting element 111 (step S30), the pulse wave measuring device waits a period of a given sampling cycle (steps S31 and S32). When sampling timing comes, an output from the light-receiving element 112 is sampled (step S33). At this time, a determination is made as to whether or not the external pulse wave sensor 110 is connected and whether or not the external pulse wave sensor 110 is put on the human body (chiefly on the thick of the finger) of the user, in accordance with a change in the output from the light-receiving element 112 immediately after emitting of the light-emitting element 111.

First, a determination is made as to whether or not a value determined by sampling the output from the light-receiving element 111 is equal to or smaller than a given threshold value (e.g., a value of 200) (step S34).

When the sampled value is equal to or smaller than the threshold value, the number of appearances of a value which is equal to or smaller than the threshold value is counted (step S35). A determination is made as to whether or not the sampled value continually remains smaller than the threshold value for a given period of time (step S36). The continuing time is determined by multiplying a count value by a sampling cycle. When the sampled value remains not smaller than the threshold value for a given period of time or longer, the pulse wave measuring device returns to a sampling standby state (step S31). In contrast, when the sampled value continually remains smaller than the threshold value for a given period of time or longer, the external pulse wave sensor 110 is determined to be connected and properly attached to a finger, and the external pulse wave sensor 110 initiates measurement (step S37).

In the meantime, when the sampled value is determined not to be equal to and smaller than the threshold value in step S34, a determination is made as to whether or not the count values that have been equal to and smaller than the threshold value thus far are equal to or less than a given value (e.g., zero or less) (step S38). When a count value is the sum of a given value and one or more (e.g., one or more) is achieved, the external pulse wave sensor 110 is determined to be connected but improperly attached to a finger (step S39). When the count value is a given value or less (e.g., zero or less), the external pulse wave sensor 110 is determined not to be connected (step S40).

When the external pulse wave sensor 110 is connected but improperly attached to a finger, a notification to the effect is sent to the user. In relation to a notification method, when the pulse wave measuring device is equipped with a liquid-crystal display, the notification is displayed on the display. When the pulse wave measuring device is equipped with a speaker, the notification is provided by means of warning sound or voice. Both the sound and the voice may also be used in combination. Vibrations caused by a vibrator may also be used alone or in combination.

In order to accurately determine whether or not the external pulse wave sensor is connected and attached, the user preferably stays quiet. Accordingly, the external pulse wave sensor connection determination section 105 may also be equipped with a motion detection section (not shown) for detecting user's motion. For instance, an acceleration sensor is preferable for the configuration of the motion detection section. When the motion detection section detects user's motion of a given level or higher in the middle of response observation of the light-receiving element 112, it is preferable not to make a determination as to connection and carry out the determination again after the motion has become smaller to a given level or less.

(Determination as to the Connection-and-Attachment of the Internal Pulse Wave Sensor)

Figure 8:
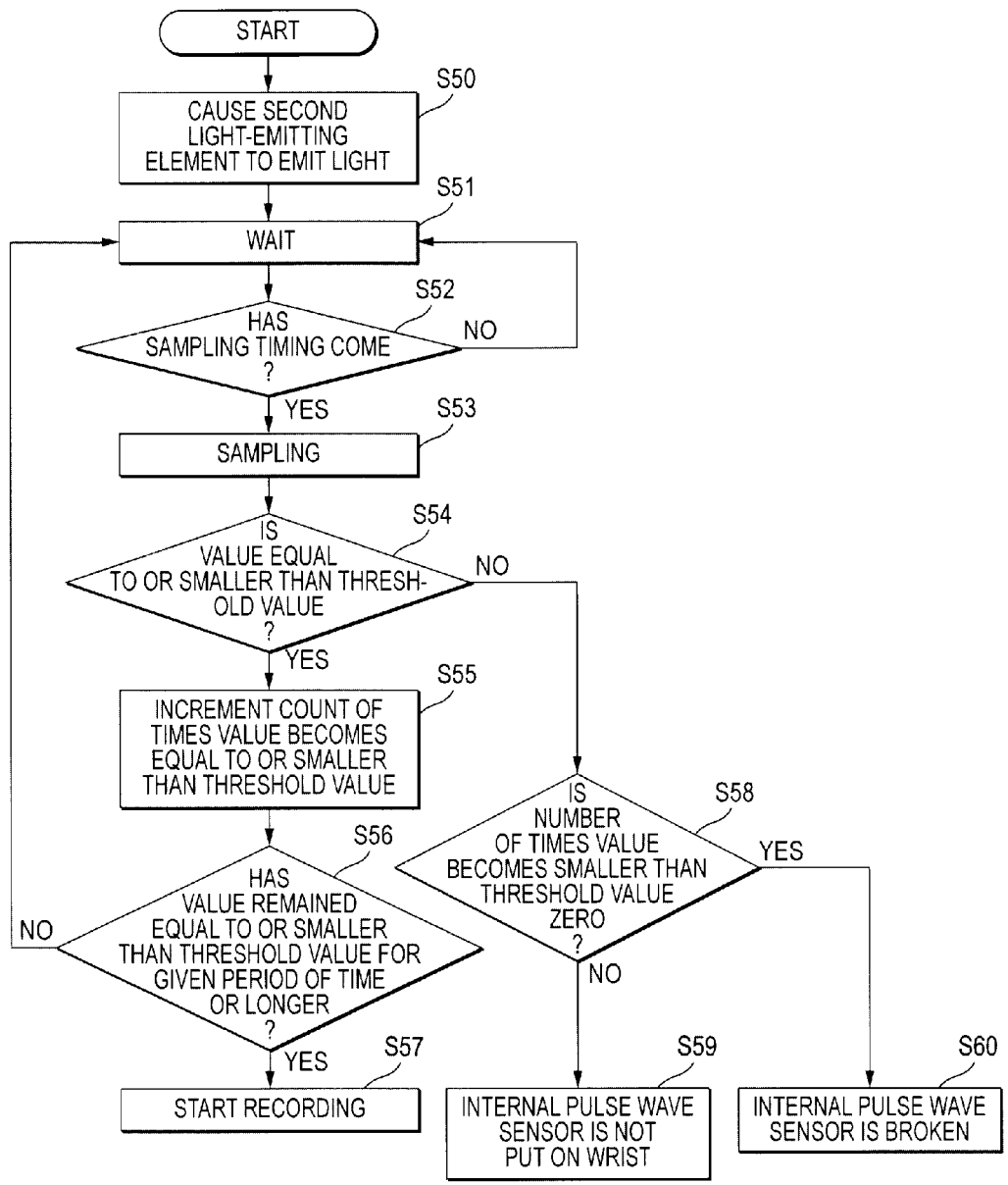
FIG. 8 is an exemplary flowchart showing processing operation of the embodiment of the present invention.

The internal pulse wave sensor attachment determination section 107 performs a determination in the same manner as does the external pulse wave sensor attachment determination section 106. Processing operation performed for determining whether or not the internal pulse wave sensor is connected and attached (step S20, and the like) will be described in detail along a flowchart shown in FIG. 8.

After emitting of the second light-emitting element 121 (step S50), the pulse wave measuring device waits a period of a given sampling cycle (steps S51 and S52). When sampling timing comes, an output from the second light-receiving element 122 is sampled (step S53). At this time, a determination is made as to whether or not the internal pulse wave sensor 120 is connected and whether or not the internal pulse wave sensor 120 is put on the human body (chiefly on the wrist) of the user, in accordance with a change in the output from the second light-receiving element 122 immediately after emitting of the second light-emitting element 121.

First, a determination is made as to whether or not a value determined by sampling the output from the second light-receiving element 121 is smaller than a given threshold value (e.g., a value of 200) (step S54).

When the sampled value is not equal to or smaller than the threshold value and when a count value achieved where the number of appearances that is equal to or smaller than the threshold value is counted is equal to or greater than the sum of the given value and one, the pulse wave measuring device main unit 100 is determined to be improperly attached (step S59). When the count value that is equal to or smaller than the threshold value is equal to or smaller than the given value (e.g., zero or less), at least one of the second light-emitting element 121 and the second light-receiving element 122 is determined that a failure, a break in a wire, faulty mounting, or the like occurs (step S60), and a notification of the failure etc. is sent to the user.

In relation to a notification method, when the pulse wave measuring device is equipped with a liquid-crystal display, the notification is displayed on the display. When the pulse wave measuring device is equipped with a speaker, the notification is provided by means of warning sound or voice. Both the display and the speaker may also be used in combination. Vibrations caused by a vibrator may also be used alone or in combination.

When the sampled value is smaller than the threshold value, the number of appearances of the sampled value that is equal to or smaller than the threshold value is counted (step S55). A determination is made as to whether or not a period of time during which the sampled value is smaller than a threshold value has continued for a given period of time (step S56). The continuing time is determined by multiplying a count value by a sampling cycle. When the period of time is not equal to or longer than the given period of time, processing returns to a sampling standby state (step S51). When the period of time is equal to or longer than the given period of time, the internal pulse wave sensor 120 initiates measurement (step S57).

(About a Response Characteristic of the Light-Receiving Element)

There is subsequently described a response characteristic of the light-receiving element achieved after control of emitting of the light-emitting element.

Figure 9:
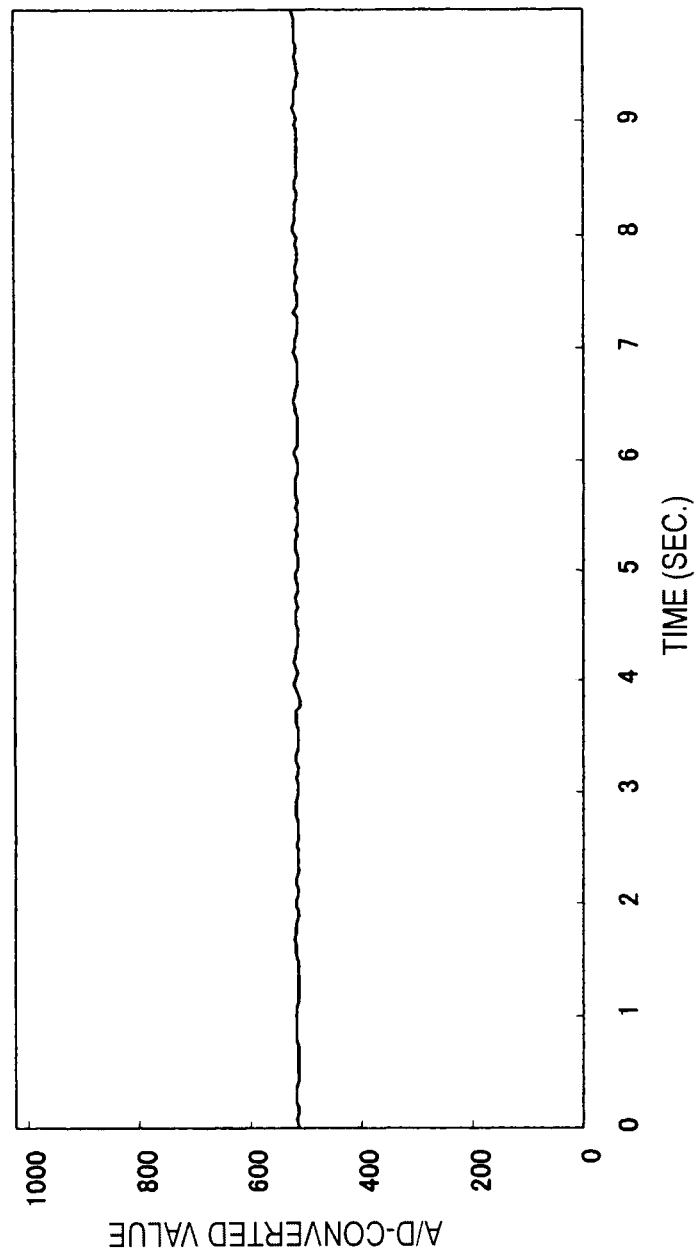
FIG. 9 is an exemplary view showing an example response of a light-receiving element produced when the external pulse wave sensor is not connected.

When the external pulse wave sensor 110 is not connected, an output from the light-receiving element 112 produced after control of emitting of the light-emitting element 111 is as shown in FIG. 9. In FIG. 9, a horizontal axis represents a time (seconds), and a vertical axis represents a value achieved after analogue-to-digital conversion of an output from the light-receiving element 112.

When the external pulse wave sensor 110 is not connected to the pulse wave measuring device main unit, an output from the light-receiving element 112 remains substantially unchanged, and noticeable changes in the output are not observed.

Figure 10:
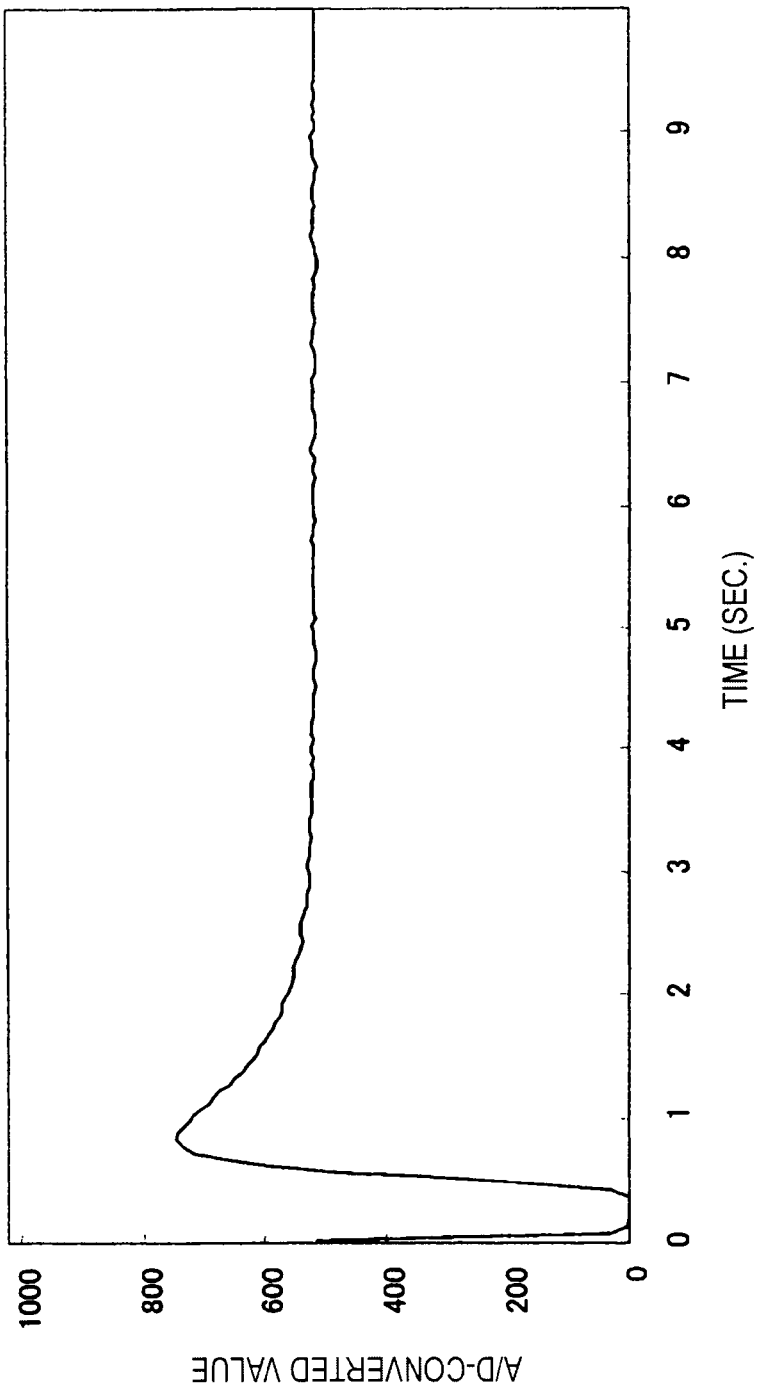
FIG. 10 is an exemplary view showing an example response of the light-receiving element produced when the external pulse wave sensor is connected.

Next, when the external pulse wave sensor 110 is connected and left in the dark, an output from the light-receiving element 112 produced immediately after control of emitting of the light-emitting element 111 is as shown in FIG. 10. This is, for instance, a case where the user measures a pulse wave immediately before going to bed in the night. As shown in FIG. 10, a transient response arose regardless of presence/absence of disturbance. Specifically, a great undershoot once arises in the output from the light-receiving element 112 during a period of only one-tenth of a second immediately after ascertainment of connection of the external pulse wave sensor 110, and the output value then greatly, sharply increases during a period of only one-third of a second. After about one second, the output reaches the maximum value. Subsequently, the output becomes gradually reduced and enters, after about three seconds, a state where no essential variations are present.

Accordingly, a given threshold value is set for an output value of the light-receiving element 111. The external pulse wave sensor connection determination section 105 can determine whether or not the external pulse wave sensor 110 is connected, according to whether or not the output value becomes smaller than the threshold value within a given period of time. Depending on a circuit configuration, there is the case where a transient response shown in FIG. 10 appears upside down. In such a case, a determination is made according to whether or not an output value has surpassed the threshold value.

When the external pulse wave sensor 110 is not put on a finger and left in the dark, a change in the output from the light-receiving element 112 appears in the same manner as shown in FIG. 10.

Figure 11:
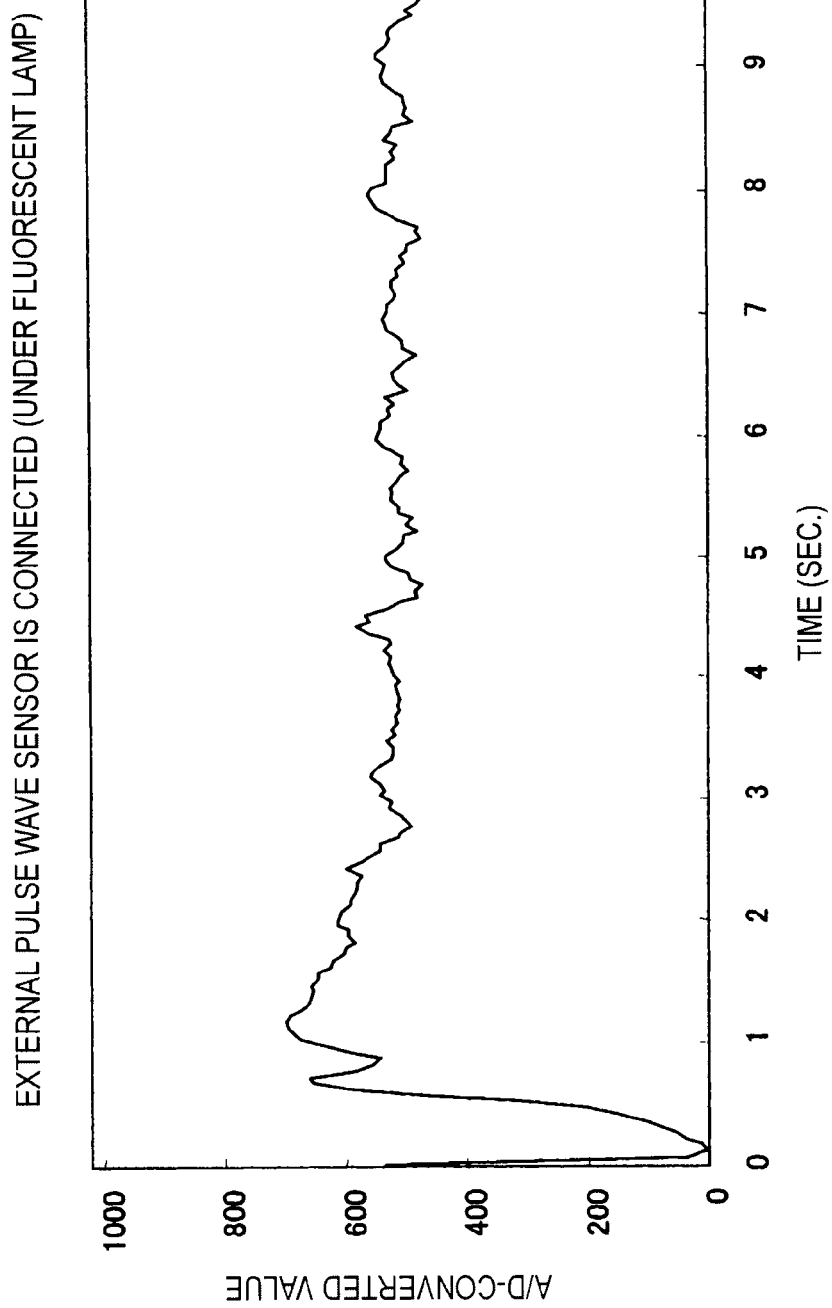
FIG. 11 is an exemplary view showing an example response of the light-receiving element produced when the external pulse wave sensor is connected.

When the external pulse wave sensor 110 is connected under a fluorescent lamp, an output from the light-receiving element 112 immediately after control of emitting of the light-emitting element 111 becomes as shown in FIG. 11; for instance, an output obtained in a case where the user connects the external pulse wave sensor 110 under the fluorescent lamp.

Even under the fluorescent lamp, a transient response arises regardless of presence/absence of disturbance. Specifically, a large undershoot once arises in an output from the light-receiving element 112 during a period of only one-tenth of a second immediately after ascertainment of connection of the external pulse wave sensor 110; the output value sharply, greatly increases within a period of only about one-half second; and the output value reaches the maximum value after about one second. Subsequently, the output value is found to gradually decrease. A variation in the output from the light-receiving element 112 acquired when the external pulse wave sensor 110 is not put on the finger and left under the fluorescent lamp appears in the same manner as does in the case shown in FIG. 11.

Figure 12:
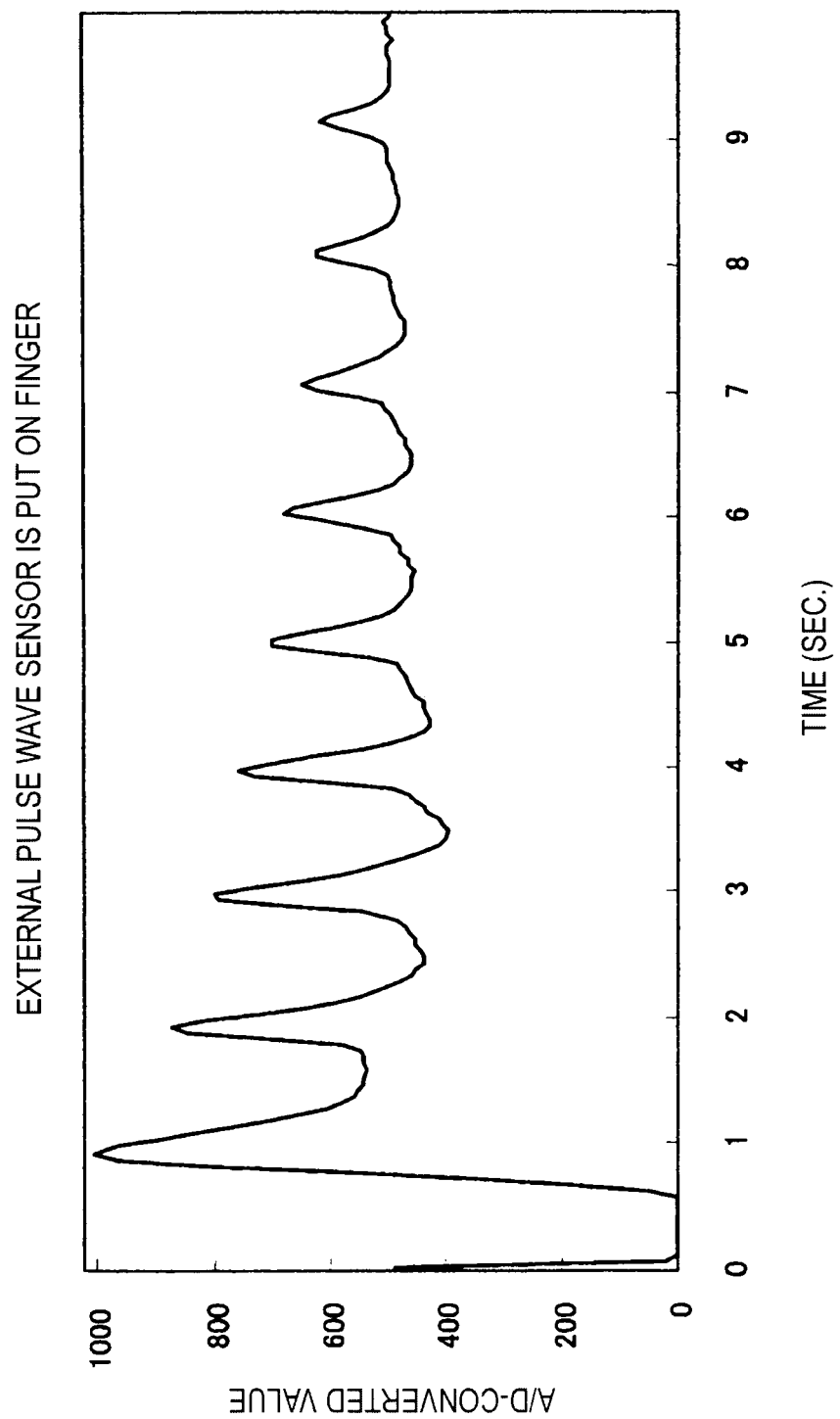
FIG. 12 is an exemplary view showing an example output from the light-receiving element produced when the external pulse wave sensor is attached to a finger.

An output from the light-receiving element 112 achieved when the external pulse wave sensor 110 is properly put on the finger is provided as shown in FIG. 12. Even in this case, a transient response arises regardless of presence/absence of disturbance. Specifically, a large undershoot once arises in an output from the light-receiving element 112 during a period of only one-tenth of a second immediately after ascertainment of attachment of the external pulse wave sensor 110; the output value sharply, greatly increases within a period of only about one-half second; and the output value reaches the maximum value after about one second. Subsequently, the output value is found to gradually decrease while pulsation is continually performed.

When the external pulse wave sensor 110 is put on a finger, the external pulse wave sensor 110 remains in close contact with the surface of the skin. Therefore, reflected light originating from the light-emitting element 111 is more intense than that acquired when the sensor is not attached, and a large transient response arises. Moreover, a duration of the transient response is longer than a duration of the transient response achieved when the sensor is not attached, without regard to the presence/absence of disturbance.

Accordingly, a given threshold value is set for an output value of the light-receiving element 112, and another threshold value is also set for a given period of time during which the output value becomes smaller than the given threshold value. When a period of time during which the output value becomes smaller than the given threshold value is longer than a given period of time, the external pulse wave sensor attachment determination section 106 determines that the external pulse wave sensor is attached. In contrast, when the period of time is shorter than the given period of time, the external pulse wave sensor attachment determination section 106 determines that the external pulse wave sensor is not attached.

The same also applies to a response characteristic of the internal pulse wave sensor 120.

[Second Embodiment]

The foregoing first embodiment utilizes a transient response of the light-receiving element occurred after activation of the light-emitting element. However, the present invention is not limited to the embodiment.

A second embodiment utilizes a plurality of observations of a response of the light-receiving element occurred after activation of the light-emitting element; for instance, two observations. Specifically, a response of the light-receiving element occurred after activation of the light-emitting element, a subsequent response of the light-receiving element occurred after deactivation of the light-emitting element, and a response characteristic of the light-receiving element acquired after re-activation of the light-emitting element are observed, whereby a determination can be made as to whether or not the external pulse wave sensor is connected to the pulse wave measuring device.

Figure 13:
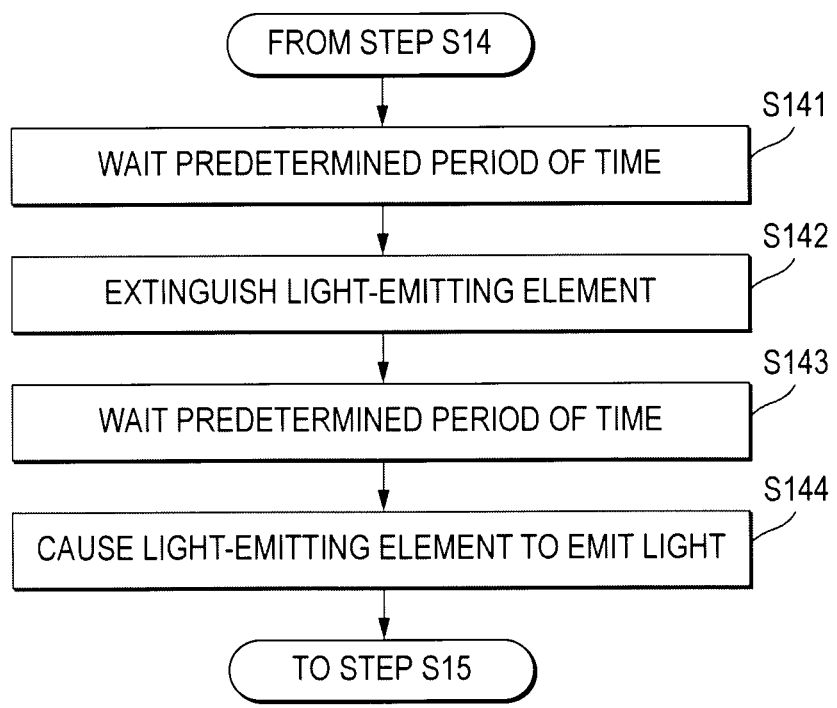
FIG. 13 is an exemplary flowchart showing processing operation achieved in a second embodiment.

Processing operation of a pulse wave measuring device of the second embodiment corresponds to processing operation represented by the flowchart shown in FIG. 6 to which a flowchart is partially added. FIG. 13 shows the flowchart to be added. Specifically, the pulse wave measuring device stays in a standby state for a given period of time. For instance, about one-half second, after foregoing processing pertaining to step S14 (step S141), and the light-emitting element is switched to the OFF state (step S142). Next, after the pulse wave measuring device stays in a standby state for a given period of time; for instance, about one-half second (step S143), the light-emitting element is again switched to the ON state (step S144). Subsequently, processing returns to previously-described step S15.

Figure 14:
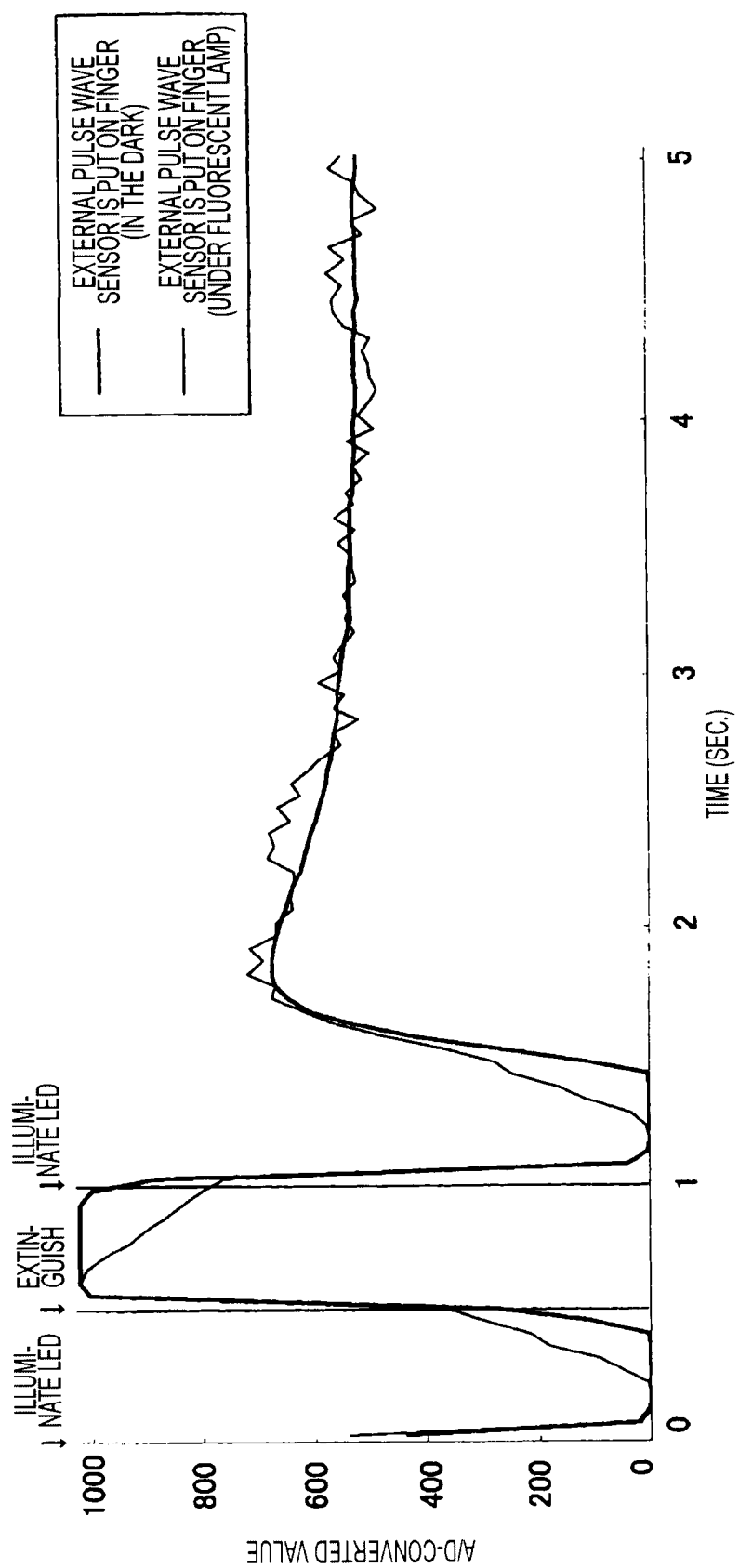
FIG. 14 is an exemplary view showing an example response of a light-receiving element produced after emitting of a light-emitting element of the second embodiment.

For instance, a response characteristic of the light-receiving element achieved in the case of the second embodiment becomes as shown in FIG. 14.

In FIG. 14, a thick solid line designates a response characteristic achieved when the external pulse wave sensor is connected in the dark but is not properly put on the user's finger. In FIG. 14, a fine solid line designates a response characteristic achieved when the external pulse wave sensor is connected under a fluorescent lamp but is not properly put on the user's finger.

In the second embodiment, a change in an analogue-to-digitally converted value is iterated, and hence a determination as to connection-and-attachment of the external pulse wave sensor becomes more accurate.

The present invention is not limited as-is to the foregoing embodiments and can be embodied in a practical stage while constituent elements are modified within the scope of the gist of the invention.

Various inventions can be conceived by appropriate combinations of the plurality of constituent elements disclosed in the embodiments. For example, some constituent elements may also be deleted from all of the constituent elements described in the embodiments. In addition, the constituent elements of the different embodiments may also be combined as necessary.

As described with reference to the embodiment, there is provided a pulse wave measuring device that enables ascertainment of connection and attachment of a pulse wave sensor, which is located outside a main unit of the device, without having a special connection mechanism.

According to the embodiment, a pulse wave measuring device to be put on a wrist like a wrist watch can detect connection/disconnection of an external pulse wave sensor, which measures a pulse wave outside a main unit, without use of a special mechanism for detecting connection, and hence a connector can be miniaturized.

What is claimed is:

1. A pulse wave measuring device comprising:
a main unit; and
an external sensor detachably connected to the main unit and that includes:
an external light-emitting module emitting light to a human body to be measured, and
an external light-receiving module receiving at least one of reflected light and transmitted light originating from the external light-emitting module and the human body to thereby perform a measurement of a pulse wave;
wherein the main unit includes:
a connector to which the external sensor is connectable;
a first controller that controls the external light-emitting module through a connection between the external sensor and the connector;
a second controller that controls the external light-receiving module through the connection between the external sensor and the connector; and
an external sensor connection determination section that determines whether the connection between the external sensor and the connector is established based on a transient response of the external light-receiving module upon an activation of the external light-emitting module and the external light-receiving module,
wherein the measurement of the pulse wave by using the external sensor is started after the external sensor connection determination section determines that the connection between the external sensor and the connector is established, wherein the main unit further includes:
an internal sensor that includes:
an internal light-emitting module emitting light to a human body be measured, and
an internal light-receiving module receiving at least one of reflected light and transmitted light originating from the internal light-emitting module to thereby perform the measurement of the pulse wave independently from the external sensor;
a third controller that controls the internal light-emitting module; and
a fourth controller that controls the internal light-receiving module,
wherein the measurement of the pulse wave by using the internal sensor is started after the external sensor connection determination section determines that the connection between the external sensor and the connector is not established.

2. The pulse wave measuring device according to claim 1, wherein the transient response includes:
a first transient response measured when both of the external light-emitting module and the external light-receiving module are activated;
a second transient response measured when, after the first transient response, the external light emitting module is inactivated; and
a third transient response measured when, after the second transient response, the external light emitting module is reactivated.

3. The pulse wave measuring device according to claim 1, wherein the external sensor connection determination section determines the connection between the external sensor and the connector according to whether or not an output from the external light-receiving module upon the activation of the external light-receiving module remains continually smaller or larger than a given threshold level for a given period of time or longer than the given period of time.

4. The pulse wave measuring device according to claim 1, wherein the external sensor is configured to be wrapped around a finger of the human body and the main unit includes a strap to be wrapped around a wrist of the human body.

* * * * *